(12) United States Patent
McFarlane

(10) Patent No.: US 10,159,426 B2
(45) Date of Patent: Dec. 25, 2018

(54) APPARATUS AND METHOD FOR SELECTING A CYCLE SHORT PAD

(71) Applicant: Endura Limited, Livingston, West Lothian (GB)

(72) Inventor: James Brown McFarlane, Edinburgh (GB)

(73) Assignee: Endura Limited, West Lothian (GB)

( * ) Notice: Subject to any disclaimer, the term of this patent is extended or adjusted under 35 U.S.C. 154(b) by 617 days.

(21) Appl. No.: 14/519,619

(22) Filed: Oct. 21, 2014

(65) Prior Publication Data

US 2015/0112632 A1    Apr. 23, 2015

(30) Foreign Application Priority Data

Oct. 21, 2013    (GB) .................................. 1318563.2

(51) Int. Cl.
     *A61B 5/103*      (2006.01)
     *A41D 1/084*      (2018.01)
     *A61B 5/00*      (2006.01)

(52) U.S. Cl.
     CPC ............ *A61B 5/1036* (2013.01); *A41D 1/084* (2013.01); *A61B 5/6895* (2013.01)

(58) Field of Classification Search
     CPC .................................................... A61B 5/1036
     See application file for complete search history.

(56) References Cited

U.S. PATENT DOCUMENTS

| | | |
|---|---|---|
| 2004/0232742 A1 | 11/2004 | Oehler |
| 2006/0218809 A1 | 10/2006 | Bird et al. |
| 2011/0059825 A1 | 3/2011 | McGown |

FOREIGN PATENT DOCUMENTS

| | | |
|---|---|---|
| DE | 202010008146 U1 | 11/2010 |
| DE | 102009045829 A1 | 4/2011 |
| EP | 1698545 A1 | 9/2006 |
| EP | 2535248 A1 | 12/2012 |
| KR | 20070038633 A | 4/2007 |
| WO | 9501302 A2 | 1/1995 |

OTHER PUBLICATIONS

European Search Report, Application No. EP14189233.1-760, dated Feb. 23, 2015.

*Primary Examiner* — Manuel A Rivera Vargas
(74) *Attorney, Agent, or Firm* — Quinn IP Law

(57) ABSTRACT

An apparatus for selecting a cycle short pad includes a saddle having pressure sensors and a processor which compares data from the pressure sensors to data stored in a database to suggest a preferred cycle short pad. The processor is connected to and, receives data generated by, the pressure sensors and produces a user pressure data set. The database is connected to the processor and includes stored pressure data sets and a cycle short pad associated with each stored pressure data set. The processor compares the user pressure data set to each stored pressure data set to identify a preferred cycle short pad. A method includes receiving pressure data from the pressure sensors in the saddle while the user cycles to produce a user pressure data set and then comparing the user pressure data set to the stored pressure data sets to select a preferred cycle short pad.

17 Claims, 2 Drawing Sheets

APPARATUS AND METHOD FOR SELECTING A CYCLE SHORT PAD

CROSS-REFERENCE TO RELATED APPLICATIONS

This application claims the benefit of Great Britain Patent Application No. GB1318563.2, filed on Oct. 21, 2013, which is hereby incorporated by reference in its entirety.

TECHNICAL FIELD

The present disclosure is related to an apparatus and method for selecting a cycle short pad.

BACKGROUND

Cycle shorts may include integrated cycle short pads to cushion the user. The pads absorb shocks and smooth pressure points when sitting on a bicycle saddle so increasing comfort for the wearer.

Different people create peak pressures on different areas on the saddle. Because of this, a number of cycle companies have released saddles of different width options. The fitting processes used to date to select the correct saddle width for a given user are crude and unreliable.

SUMMARY

The present disclosure relates to an apparatus for selecting a cycle short pad. More particularly, but not exclusively, the present disclosure relates to an apparatus for selecting a cycle short pad comprising a saddle which in turn comprises a plurality of pressure sensors and a processor which compares the data from the pressure sensors to data stored in a database to suggest a preferred cycle short pad. The present disclosure also relates to a method of selecting a cycle short pad. More particularly, but not exclusively, the present disclosure relates to a method of selecting a cycle short pad comprising the steps of receiving pressure data from a plurality of pressure sensors in a saddle while a user cycles to produce a user pressure data set and then comparing the user pressure data set to a plurality of stored pressure data sets to select a preferred cycle short pad.

In a first aspect of the disclosure, an apparatus is provided for selecting a cycle short pad including a saddle, a processor, and a database. The saddle includes a plurality of pressure sensors adapted to measure the pressure applied to the saddle by a user at a plurality of spaced apart points on the saddle. The processor is connected to the pressure sensors adapted to receive the data generated by the pressure sensors and produce a user pressure data set. The database is connected to the processor. The database includes a plurality of stored pressure data sets and a cycle short pad associated with each stored pressure data set. The processor is adapted to compare the user pressure data set to each of the stored pressure data sets of the database to identify a preferred cycle short pad.

The apparatus allows a far more accurate and less subjective choice of cycle short pad to be made so increasing user comfort. Preferably, the saddle comprises a covering sleeve, the pressure sensors being arranged in the covering sleeve. Preferably, the processor is wirelessly connected to the pressure sensors, preferably by Bluetooth®. Preferably, the user pressure data set and each of the stored pressure data sets is a map of peak pressure as a function of position on the saddle. Preferably, the processor employs a best fit algorithm to compare the user pressure data set to each of the stored pressure data sets.

Preferably, the best fit algorithm calculates a pressure variation score for each stored pressure data set, the cycle short pad associated with the stored pressure data set having the smallest pressure variation score being the preferred cycle short pad. The pressure variation score for a stored pressure data set is calculated by determining for each point in the stored pressure data set the difference between the stored pressure at that point and the pressure at the corresponding point in the user data set, and summing the modulus of the differences over the whole stored pressure data set to produce the pressure variation score.

In a further aspect of the disclosure, there is provided a method of selecting a cycle short pad. The method includes the steps of arranging a user on a saddle, the saddle comprising a plurality of pressure sensors arranged at a plurality of spaced apart points on the saddle; receiving data from the pressure sensors whilst the user cycles to produce a user pressure data set; and comparing the user data set to each of a plurality of stored pressure data sets, each stored pressure data set having a cycle short pad associated therewith, to identify a preferred cycle short pad.

Preferably, the user pressure data set and each of the stored pressure data sets is a map of peak pressure as a function of position on the saddle.

Preferably the comparison step comprises employing a best fit algorithm to compare the user pressure data set to each of the stored pressure data sets.

The above features and advantages and other features and advantages of the present teachings are readily apparent from the following detailed description of the best modes for carrying out the present teachings when taken in connection with the accompanying drawings.

DETAILED DESCRIPTION

Figure 1:
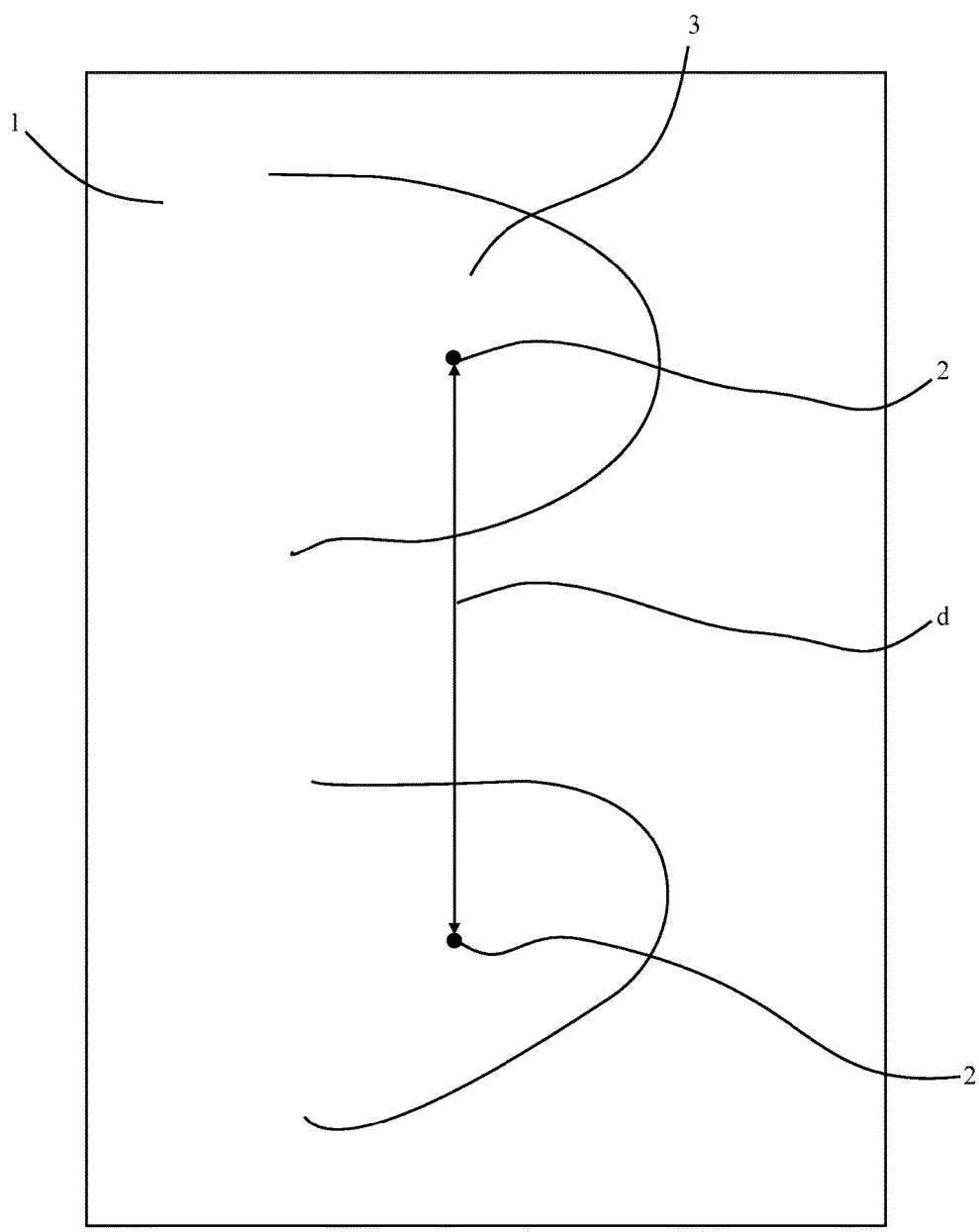
FIG. 1 shows, in schematic form, a known method of selecting a cycle saddle for a user.

Referring to the drawings, wherein like reference numbers refer to like components throughout the several Figures, an apparatus for selecting a cycle short pad is shown schematically in FIG. 1.

Different people create different pressures on the saddle in different areas due to a combination of their sit riding position, bone width geometry (the distance/width between their sit bones), their pelvic flexibility and their adopted riding position, ranging from an upright position for relaxed riding through to an aggressive posture for time trials and racing for aerodynamic advantage. The combination of these factors creates a pressure profile on the saddle for any given rider.

Because of this over recent years a number of cycle companies have released a number of different width options of saddles of the same model. Shown schematically in FIG. 1 is the method used to date to correctly prescribe the correct width of cycle saddle for a user.

The user is asked to sit on a chair or bench that has a flat plate 1 with either a piece of memory foam or some other flat plate with a sealed substance that is parted due to pressure created by the sit bones. The consumer is asked to approximate the position that they might adopt when on a bicycle and the lateral distance 'd' between the two center points 2 of impression 3 on the memory foam (or other means that shows pressure points) is then measured as the sit bone width. The preferred saddle width is then prescribed.

There are numerous fundamental flaws with this approach. Firstly, the user is sat, or otherwise seated, on a bench with both feet symmetrically positioned. However, when cycling, one leg is always out of synchronization with the other creating a different asymmetric pressure on the saddle.

Secondly, the user is asked to lean forward to the degree that they do when cycling but is asked to do so whilst not being on their bike and so has no familiar frame of reference as to what their normal riding position is.

Thirdly, the plate 1 the user sits on is flat and is not shaped like a bicycle saddle. It therefore creates a completely different pressure profile than what would be created if the same person were to sit on a bicycle saddle. The distances between the peak pressure points created by sit bones on a saddle are substantially different from those generated by the same user when seated on a flat measurement plate.

Finally, the actual peak pressure point generated by each sit bone on the saddle typically does not lie at the center of the pressure depression in the memory foam. Instead it lies off center from the center of the depression. This means that the distance measured between the centers of the two recorded depressions as used in the method described above provide sit bone widths that are substantially different from the distance measured between the real peak pressure points of each sit bone. This difference is typically of the order 8 to 10% which is materially incorrect.

The process described above could also be used for prescribing the correct width of cycle pad for a user. However, due to the shortcomings of the method described above, the method would be inaccurate.

Figure 2:
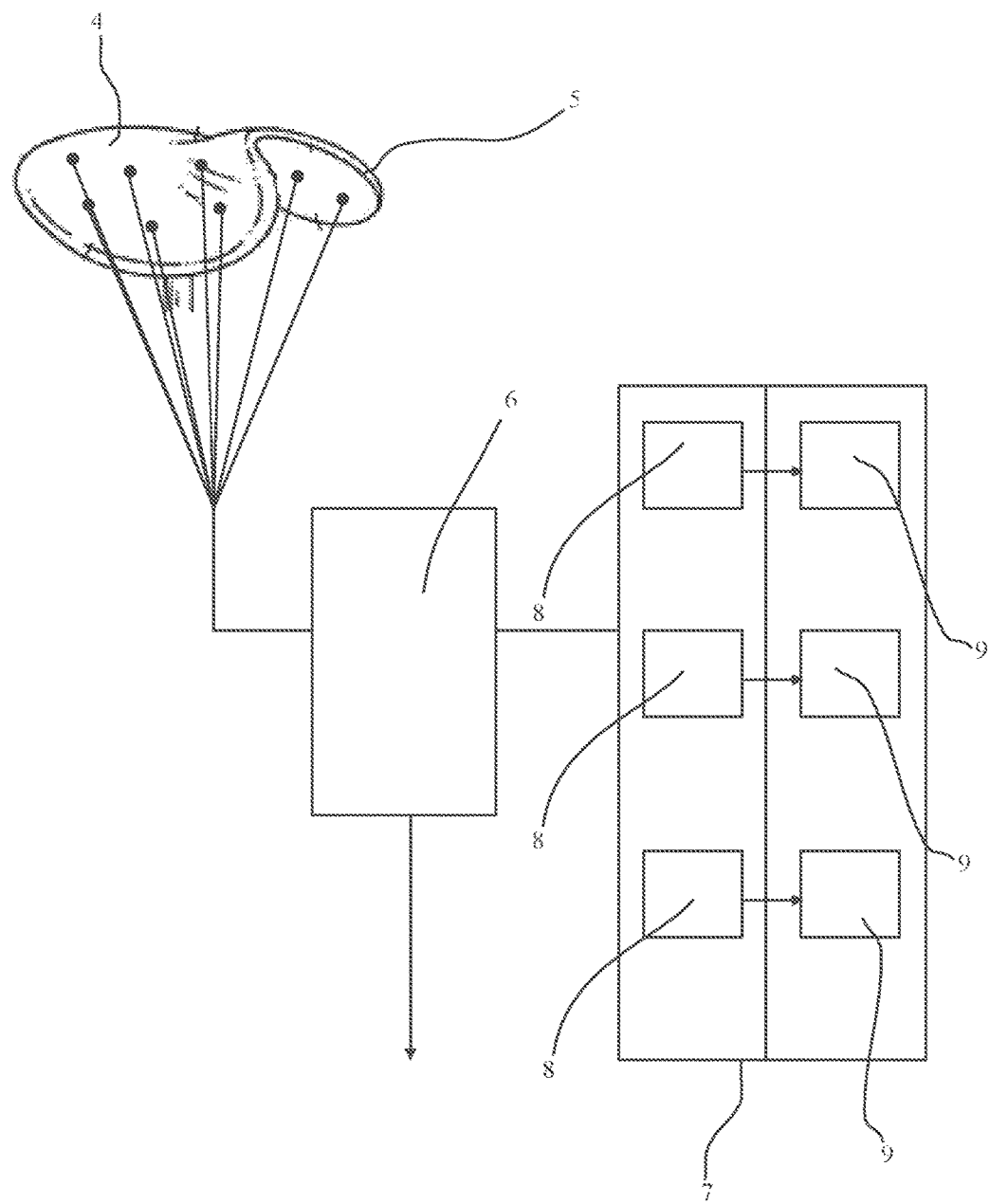
FIG. 2 shows, in schematic form, an apparatus according to the disclosure.

Shown in FIG. 2 is an apparatus for selecting a cycle short pad according to the disclosure. A cycle short pad is a pad worn in cycle shorts or which is an integral part of cycle shorts. The apparatus comprises a saddle 4 comprising a plurality of pressure sensors 5 at spaced apart points in its upper surface. The pressure sensors measure the pressure exerted by the user on the upper surface of the saddle 4. In this embodiment, the pressure sensors 5 are an integral part of the saddle 4. In an alternative embodiment, the saddle 4 comprises a removable sleeve, and the pressure sensors 5 are contained in the sleeve 4.

Connected to the pressure sensors 5 is a processor 6. This may be a wired connection or alternatively may be a wireless connection such as Bluetooth®.

Further connected to the processor 6 is a database 7. The database 7 contains a plurality of stored pressure data sets 8. Each stored pressure data set 8 comprises a plurality of pressure readings, each pressure reading corresponding to one of the pressure sensors in the saddle 4. Associated with each stored pressure data set 8 is a cycle short pad 9.

In use a user is arranged on the saddle 4. The user wears an unlined cycle short, typically a Lycra® skin fit short or the like. The user then cycles in their normal cycling position whilst the pressure sensors 5 record pressure data. This pressure data is then passed to the processor 6 where is it processed into a user pressure data set. The user pressure data set comprises a plurality of pressure readings, one corresponding to each pressure sensor 5. In this embodiment the user pressure data set is the user's natural peak dynamic saddle pressure profile ('NPDSP') This is the map of the peak pressures generated across the saddle 4 whilst the user cycles (or in other words, each pressure point in the user pressure data set is the peak pressure measured at the point on the saddle 4 corresponding to that pressure point in the user pressure data set). Differences in absolute pressure caused by differences in user weight can be normalized. This is typically done by using pressure variation across the pressure sensors 5 as percentages measured against a base pressure rather than using absolute pressures.

Each stored pressure data set 8 in the database 7 is also a (normalized) natural peak dynamic pressure profile. The processor 6 compares the user pressure data set to each of the stored pressure data sets 8 using a best fit algorithm to determine which stored pressure data set 8 is the best fit to the user pressure data set. The processor 6 then identifies the cycle short pad associated with the best fit stored pressure data set 8 and returns this as the preferred cycle short pad 9.

In this embodiment the best fit algorithm operates as follows. The best fit algorithm calculates a pressure variation score for each stored pressure data set 8. The cycle short pad associated with the stored pressure data set 8 having the smallest pressure variation score is the preferred cycle short pad returned by the processor 6 to the operator. The pressure variation score for a pressure data set is calculated by a two step process. Firstly, for each point in the stored pressure data set 8 the difference between the stored pressure at that point and the pressure at the corresponding point in the user data set is calculated. Then, the modulus of these differences is summed over the whole pressure data set to produce the pressure variation score.

The database 7 needs to be populated with stored pressure data sets 8 and associated choices of cycle short pads 9. In order to do this, a plurality of test users with varying sit bone geometries are employed to create a wide range of NPDSPs. Each test user cycles on the saddle 4 in unpadded shorts and their natural peak dynamic saddle pressure profile is stored as a stored pressure data set 8. The test user then cycles on the apparatus again wearing shorts or other legwear containing each of the available cycle short pads. The results of these further tests are then analyzed (typically by hand or by use of the apparatus to identify the pad option that results in the lowest peak pressures for the test rider in the riding position that corresponds to each NPDSP) to determine which is the best cycle short pad for that particular user. That cycle short pad is then associated with the original natural peak dynamic saddle pressure profile stored in the database 7.

In an alternative embodiment the data provided by the pressure sensors 5 is already in a form suitable for use as a user pressure data set. For example, each pressure sensor 5 may only provide the peak pressure recorded by that pressure sensor to the processor 6. This array of data is suitable for use as a user pressure data set 8 by the processor 6 without the need for any pre-processing.

In alternative embodiments, the pressure data sets may be other than the natural peak dynamic saddle pressure profile. Each point in the pressure data set could for example correspond to the variation in pressure recorded at the corresponding point on the saddle 4.

Similarly, in alternative embodiments a variety of different best fit algorithms could be employed. As an example, the best fit algorithm may calculate the root mean square difference between each data point in the user data set and stored data set 8 to produce a variation score.

While the best modes for carrying out the many aspects of the present teachings have been described in detail, those familiar with the art to which these teachings relate will recognize various alternative aspects for practicing the present teachings that are within the scope of the appended claims.

The invention claimed is:

1. An apparatus for selecting a cycle short pad comprising:
   a saddle with a plurality of pressure sensors adapted to measure pressure applied to the saddle by a user at a plurality of spaced apart points on the saddle;
   a processor connected to the pressure sensors adapted to receive data generated by the pressure sensors and produce a user pressure data set;
   a database connected to the processor, the database having a plurality of stored pressure data sets and a cycle short pad associated with each stored pressure data set;
   the processor being adapted to compare the user pressure data set to each of the stored pressure data sets of the database to determine a corresponding one of the stored pressure data sets;
   the processor being adapted to identify a preferred cycle short pad associated with the corresponding one of the stored pressure data sets; and
   the processor being adapted to direct the user to the preferred cycle short pad associated with the corresponding one of the stored pressure data sets.

2. An apparatus as claimed in claim 1, wherein the saddle comprises a covering sleeve, the pressure sensors being arranged in the covering sleeve.

3. An apparatus as claimed in claim 2, wherein the processor is wirelessly connected to the pressure sensors, preferably by Bluetooth®.

4. An apparatus as claimed in claim 3, wherein the processor employs a best fit algorithm to compare the user pressure data set to each of the stored pressure data sets.

5. An apparatus as claimed in claim 2, wherein the user pressure data set and each of the stored pressure data sets is a map of peak pressure as a function of position on the saddle.

6. An apparatus as claimed in claim 2, wherein the processor employs a best fit algorithm to compare the user pressure data set to each of the stored pressure data sets.

7. An apparatus as claimed in claim 1, wherein the processor is wirelessly connected to the pressure sensors, preferably by Bluetooth®.

8. An apparatus as claimed in claim 7, wherein the user pressure data set and each of the stored pressure data sets is a map of peak pressure as a function of position on the saddle.

9. An apparatus as claimed in claim 7, wherein the processor employs a best fit algorithm to compare the user pressure data set to each of the stored pressure data sets.

10. An apparatus as claimed in claim 1, wherein the user pressure data set and each of the stored pressure data sets is a map of peak pressure as a function of position on the saddle.

11. An apparatus as claimed in claim 10, wherein the best fit algorithm calculates a pressure variation score for each stored pressure data set, the cycle short pad associated with the stored pressure data set having the smallest pressure variation score being the preferred cycle short pad, the pressure variation score for a stored pressure data set being calculated by
    (i) determining for each point in the stored pressure data set the difference between the stored pressure at that point and the pressure at the corresponding point in the user data set; and,
    (ii) summing the modulus of the differences over the whole stored pressure data set to produce the pressure variation score.

12. An apparatus as claimed in claim 1, wherein the processor employs a best fit algorithm to compare the user pressure data set to each of the stored pressure data sets.

13. A method of selecting a cycle short pad comprising the steps of:
    arranging a user on a saddle, the saddle comprising a plurality of pressure sensors arranged at a plurality of spaced apart points on the saddle;
    receiving data from the pressure sensors whilst the user cycles;
    processing the data into a user pressure data set;
    comparing the user pressure data set to each of a plurality of stored pressure data sets to determine a corresponding one of the stored pressure data sets, each stored pressure data set having a cycle short pad associated therewith;
    identifying a preferred cycle short pad associated with the corresponding one of the stored pressure data sets; and
    directing the user to the preferred cycle short pad associated with the corresponding one of the stored pressure data sets.

14. A method as claimed in claim 13, wherein the user pressure data set and each of the stored pressure data sets is a map of peak pressure as a function of position on the saddle.

15. A method as claimed in claim 14, wherein the comparison step comprises employing a best fit algorithm to compare the user pressure data set to each of the stored pressure data sets.

16. A method as claimed in claim 13, wherein the comparison step comprises employing a best fit algorithm to compare the user pressure data set to each of the stored pressure data sets.

17. An apparatus for selecting a cycle short pad for a user, the apparatus comprising:
    a saddle with a plurality of pressure sensors adapted to measure pressure applied to the saddle by a user at a plurality of spaced apart points on the saddle, as the user peddles and is not wearing a cycle short pad;
    a processor connected to the pressure sensors adapted to receive data generated by the pressure sensors and produce a user pressure data set;
    a database connected to the processor, the database having a plurality of stored pressure data sets and a cycle short pad associated with each stored pressure data set;
    wherein each of the plurality of stored pressure data sets is associated with a preferred cycle short pad selected from a plurality of cycle short pads that provides the lowest peak pressures
    the processor being adapted to:
        receive data generated by the pressure sensors and produce a user pressure data set, in response to the user being arranged on the saddle;
        compare the user pressure data set to each of the stored pressure data sets of the database to determine a pressure variation score for each of each stored pressure data set;
        identify the stored pressure data set associated with the lowest pressure variation score as a preferred cycle short pad associated; and
        direct the user, who peddled while not wearing a cycle short pad, to the identified preferred cycle short pad.

* * * * *